United States Patent [19]
Hayes et al.

[11] Patent Number: 5,952,239
[45] Date of Patent: Sep. 14, 1999

[54] CYTOLOGY CHAMBER WITH PORT TO RECEIVE COLLECTION BOTTLE AND METHOD OF USE

[75] Inventors: William J. Hayes, Edgeworth, Pa.; Daniel R. Thornton, Golden, Colo.

[73] Assignee: Shandon, Inc., Pittsburgh, Pa.

[21] Appl. No.: 08/873,708

[22] Filed: Jun. 12, 1997

[51] Int. Cl.$^6$ ........................................................ G01N 1/28
[52] U.S. Cl. ............................... 436/177; 436/45; 436/46; 436/178; 422/72; 422/101; 422/102; 427/2.11; 427/2.13
[58] Field of Search ................................ 436/45, 46, 174, 436/177, 178; 422/72, 100, 101, 102; 494/16, 17, 20; 210/780–782, 787; 427/2.11, 2.13; 435/288.1, 307.1, 308.1, 309.1

[56] References Cited

U.S. PATENT DOCUMENTS

| | | | |
|---|---|---|---|
| 4,391,710 | 7/1983 | Gordon | 210/361 |
| 4,678,559 | 7/1987 | Szabados . | |
| 4,678,579 | 7/1987 | Griffin | 210/477 |
| 4,705,630 | 11/1987 | Gordon et al. . | |
| 4,853,188 | 8/1989 | Toya | 422/104 |
| 5,470,758 | 11/1995 | Hayes | 436/177 |

OTHER PUBLICATIONS

Webster's Ninth New Collegiate Dictionary, Merriam Webster (1987) p. 808, 1987.

*Primary Examiner*—Jan Ludlow
*Attorney, Agent, or Firm*—John E. Reilly

[57] ABSTRACT

There is provided a method and system for transferring biological material samples from the point of collection to a chamber for placement into a centrifuge for processing and analysis. A container is used to hold the sample from the point of collection and during transport to a sample chamber which is placed into the centrifuge. The container is provided with a threaded open end, the threads being complementary with screw threads on a lid and also with threads around a port in the chamber. Thus, the user collects the sample, places it within the container, and engages the lid to close the open end of the container. The container is transported to the laboratory, where the lid is removed, and the threads on the container engaged with the threads on the chamber to attach the container to the chamber. The container is then inverted to permit the sample to pass from the container into the chamber. The chamber may then be placed into a known centrifuge for processing. The system and apparatus are suited for the use of a curette as the tool for collecting the sample, and permit the sample-bearing curette to be conveyed in the container without contamination from the point of collection to the laboratory centrifuge. A system of notches and keys are provided to align a filter card and slide at the discharge end of the chamber and promote uniform filtering action.

18 Claims, 1 Drawing Sheet

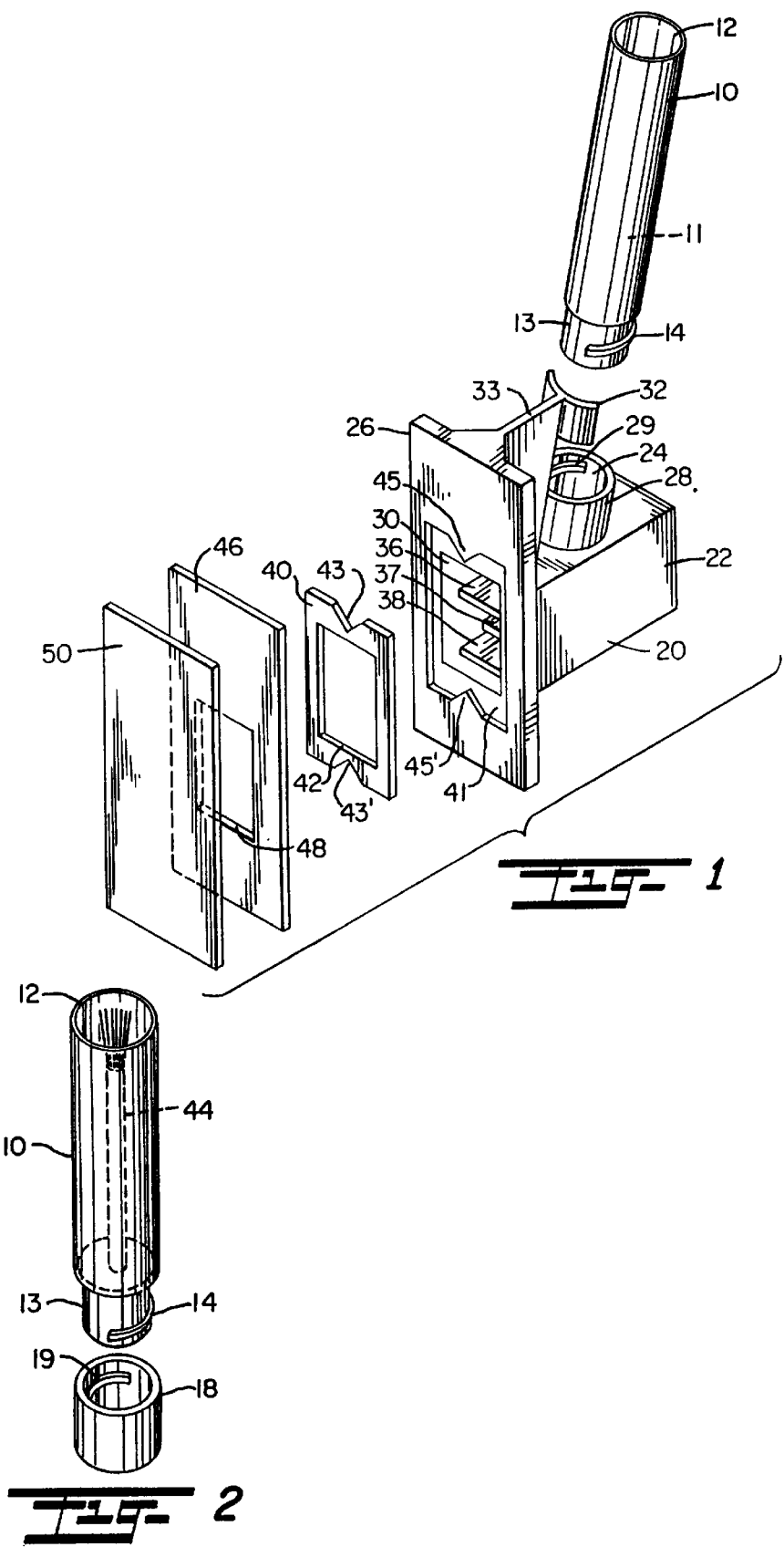

CYTOLOGY CHAMBER WITH PORT TO RECEIVE COLLECTION BOTTLE AND METHOD OF USE

BACKGROUND AND FIELD OF THE INVENTION

The invention relates to cytocentrifuge sample chambers, and more particularly to an improved cytology sample chamber with port to receive a collection bottle or container, and a method for using the same to transfer biological material from a collection tool or container to the sample chamber for analysis.

Medical diagnostic processes commonly include collecting biological material specimens from patients for laboratory analysis. Biological materials subject to collection and analysis include, but are not limited to, blood, saliva, urine, epithelial smears, semen, and the like. In nearly all instances of specimen collection and analysis, it is necessary to transport the material specimen from the point of collection to the analytical laboratory, which may involve conveying the specimen a considerable distance through a large medical center complex. Occasionally, the specimen is collected in a clinic or physician's office remotely located from the laboratory, which may involve a jostling trip of hours or days from the point of collection to the point of analysis.

Additionally, and particularly in the case of epithelial smears, such as pap smears, current specimen collection practices involve one or more instances of shifting the collected material from one surface or container to another surface or container. Samples of epithelial tissue commonly are retrieved from the patient's body using some type of curette, such as a specialized swab, spoon, brush, or spatula. In this disclosure, "curette" means any tool adapted for collecting epithelial and similar solid or semi-solid tissues from a patient's body. Typically, for example, a pap smear is taken using a specialized long-handled swab or brush. The delicate bristles of the brush are gently scraped or daubed across the uterine lining to collect on the bristles a sample of uterine tissue. The bristles are then wiped across a glass slide to prepare a smear for microscopic observation and other evaluation.

Serum samples, such as blood, meningeal fluid, and some biopsies, typically are extracted from the body using needle syringes, and are then emptied from the syringe into a container for laboratory handling. Saliva and urine samples are more readily collected, but may also involve the passage of the body fluid from one collection container to one or more other containers for processing.

Laboratory analysis of collected biological material frequently involves the use of a cytocentrifuge for separating fluid samples into various constituent components. A general description of the centrifugation process, and a suitable apparatus for accomplishing centrifugation of biological fluid samples, is contained in U.S. Pat. No. 5,470,758 to Hayes, assigned to the assignee of this application, the disclosure of which is hereby incorporated by reference. The apparatus of the '758 patent may readily be adapted for use in practicing the present invention. Other background references providing details of cytocentrifuge construction and operation, and some of the advantageous and disadvantages presented in the art, include U.S. Pat. No. 4,853,188 to Toya, No. 4,678,579 to Griffin, and No. 4,391,710 to Gordon, the respective disclosures of which also are incorporated by reference.

Current methods of collecting and analyzing biological materials unfortunately present opportunities for contamination, spillage or, rarely, mis-identification of a specimen, particularly when multiple surfaces and/or containers are serially employed to convey a specimen to the laboratory centrifuge. Each point of transfer, such as from curette to slide, or from pipette to centrifuge sample chamber, poses some risk of specimen loss or contamination. Specifically, current centrifugation methods and devices commonly require more than one material transfer to place the specimen into a sample chamber in the cytocentrifuge. The present invention reduces the number of biological material transfers needed to move a specimen from patient to laboratory cytocentrifuge, thus improving the reliability of analytical results and promoting efficiency in cytocentrifuge use.

SUMMARY OF THE INVENTION

The invention allows the user to transfer a biological material sample from the point of collection to the laboratory centrifuge with substantially decreased risk of contamination or confusion. A container receives and holds the sample, and is provided with a lid for sealed closure of the container. The chamber, which is to be placed within the centrifuge, is provided with an inlet. The open end of the container is engageable with the sample chamber so as to place the open end of the container in communication with the inlet. The sample such as urine may be placed directly within the container, or a small curette may be used to collect the sample and the curette bearing the sample placed in the container. The lid secures the open end of the container, and the container is transported to the laboratory. The lid is there removed and the container is attached to the container at the inlet. With the container attached to the chamber at the inlet, the chamber and the container are inverted to permit the sample to pass from the container, through the inlet, and into the chamber. The chamber, with the container still attached, may then be placed within the centrifuge.

An object of the invention is to provide a system for transferring biological material samples to a chamber for centrifugation while minimizing the opportunity for sample contamination.

An advantage of the invention is that a sample is moved from the point of collection to the laboratory centrifuge without the use of intermediate containers, surfaces, or transfer steps.

Another advantage of the invention is that it is useable in connection with known centrifuge devices.

In accordance with the present invention, there is provided a method of transferring biological material sample to a cytological centrifugation sample chamber for analysis, comprising providing a container having an open end, depositing the sample within the container, supplying an inlet in the sample chamber, introducing means for securing the open end of the container to the chamber in communication with the inlet, securing the container to the chamber at the inlet, and permitting the sample to pass from the container and into the chamber. The means for securing comprises means for engaging the open end to align it with the inlet, and the method further includes centrifuging the sample chamber with the container secured thereto. In the preferred method, the container has a threaded open end, and the method includes supplying a lid having threads engageable with the threaded open end. The preferred method further comprises screwing the lid onto the open end of the container subsequent to depositing the sample within the container. Depositing the sample within the container comprises collecting the sample upon a curette and placing the curette within the container. The method preferably also comprises placing a liquid into the container prior to securing the container to the chamber. The means for securing comprises supplying on the chamber threads engageable with the threads on the threaded open end. In the preferred method, securing the container comprises screwing the chamber onto the open end of the container, and permitting the sample to pass from the container comprises allowing the liquid to flow through the inlet into the chamber. The preferred method further comprises providing a filter card having at least one notch therein, furnishing a key upon the chamber, and aligning the notch with the key, and placing said filter card between a gasket and the chamber.

Also according to the present invention, there is provided a system for transferring a biological material sample to a cytological centrifugation sample chamber, wherein the chamber includes an inlet at one end and a discharge opening in communication with a microscope slide, the improvement comprising a container having an openable end for placing the sample in the container, and means for introducing the sample from the container through the inlet into the chamber. The inlet preferably is provided with means for securing a lid thereto. The preferred means for securing includes threads on an openable end, and the lid comprises threads engageable with the threads on the openable end. The preferred system further includes a curette disposable within the container. The invention also includes a system wherein the container is inverted with the openable end in threaded engagement with a port on the inlet and wherein the container inclines upwardly from the chamber.

Also in accordance with the present invention there is provided an improvement in a system for transferring biological material sample to a cytological centrifugation sample chamber of the type having an inlet at one end and a discharge opening in communication with a microscope slide, the improvement comprising a container having an open end, a lid for removably closing the open end, complementary screw threads upon the container and upon the lid, and an inlet port in the sample chamber including screw threads complementary to the threads on the container, and a solution and a curette containing the sample disposable within the container whereupon removal of the lid and threaded engagement of the port with the container, the sample flows with the solution into the chamber. This preferred system further comprises a filter card having at least one notch therein, a key upon the chamber and alignable with the notch, and a gasket, wherein the filter card is disposed between the gasket and the chamber.

The above and other objects of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 1 is an exploded perspective view of a preferred embodiment of the apparatus of the invention showing the container attachable to the sample chamber; and FIG. 2 is a perspective view of a sample container component of a preferred embodiment of the apparatus of the invention with a curette shown inside the container.

DETAILED DESCRIPTION OF A PREFERRED EMBODIMENT

The invention relates to a method and system for transferring biological material from a collection device to a cytological centrifugation sample chamber. The invention finds beneficial utility in the collection and analysis of biological materials of nearly any type, including body fluids such as blood or urine, but is particularly well-suited for use in transferring epithelial samples, such as specimens taken from a patient's uterus, from a curette to a cytocentrifuge sample chamber.

FIG. 1 illustrates that the apparatus of the invention broadly comprises a sample bottle or container 10 useable in conjunction with a sample chamber 20, filter card 40, and gasket 46. Trie sample chamber 20 is utilized in a cytocentrifuge such as that described in U.S. Pat. No. 5,470, 758. The sample chamber 20 preferably is a unitary body for receiving and holding a liquid sample of biological material, such as urine or an epithelial sample suspended in a solution 11. The chamber 20 preferably is molded from a plastic inert to conventional biological material samples and solutions. The holding portion 22 of chamber 20 is supplied with an inlet 24 having a port 28 inclining upwardly and rearwardly from the upper end of the chamber 20 and through which a fluid sample may pass into the interior of the holding portion 22. The sample chamber 20 also features a flange 26 comprising a flat rigid strip of plastic having length and width dimensions approximately equaling the corresponding dimensions of a conventional microscope slide 50. The flange 26 supports the holding portion 22 while the chamber 20 is within the cytocentrifuge, and provides a surface against which the cytocentrifuge holder clip or clamp presses to hold the chamber 20 and gasket 46 against the microscope slide 50 and in position within the centrifuge (also not shown).

The inlet 24 preferably is surrounded by an upstanding, rigid, generally tubular port 28, the interior surface of which is furnished with screw threads 29 for removable attachment of the sample container 10 as shall be further described. The interior passage of the port 28 accordingly communicates directly with the interior of the holding portion 22 via the inlet 24.

Flange 26 also provides support for the container brace 32 by means of the intermediate vertical gusset 33 extending from the back surface of the flange 26 and upward from the top of the holding portion 22. The container brace 32 preferably has a shape corresponding generally to the exterior contour of the sample container 10, for example a cylindrical container 10 suggests the use of an arcuate brace 32 having a radius substantially equaling the radius of the container 10.

The flange 26 has a discharge opening 30 therethrough from the holding portion 22. The holding portion 22 is substantially similar in shape and function, preferably including baffle plates 36, 37,38, to the holding portion of the sample chamber described in U.S. Pat. No. 5,470,758, to which reference may be had for additional detail, but which defines a tortuous path for advancement of the sample through the chamber.

The container 10 preferably is a cylindrical tube of inert plastic, clear or opaque, but alternatively may also be fashioned from stainless steel or glass depending upon particular usage. Container 10 has closed bottom end 12 and openable top end 13. As seen in the figures, the exterior circumference of the top 13 of the container 10 preferably is provided with screw threads 14 complementing the screw threads 19 within the interior of a supplied lid 18, so that the lid 18 may be secured to the top 13 of the container 10. The lid 18 therefore may be releasably secured to the container 10 to provide a sealed closure of the container 10. The invention may be adapted to incorporate alternative, equivalent means for releasably securing the lid to the container, such as a frictionally inserted cork or the like.

Notably, the top 13 of the container 10 has an exterior diameter substantially corresponding to the inside diameter of the port 28 so that the top of the container is insertable into the port, as suggested by FIG. 1, to place the open top of the container 10 in communication with the inlet 24 of the holding portion 22 with the container inclining upwardly and rearwardly therefrom. The screw threads 14 on the container 10 complement and engage with the threads 29 in the port 28 on the sample chamber 20, so that the container 10 may be sealably attached to the sample chamber 20. Alternative embodiments of the invention may include other functional means for sealably attaching the container 10 to the chamber 20. For example, a compressible gasket may be disposed about the exterior of the top 13 of the container 10 to permit a frictional, sealed, cork-like insertion of the container into a corresponding port 28 or cavity on the chamber 20.

The system of the invention preferably includes a curette 44 for collecting biological specimens from a patient and placing them within the container 10. Illustrated is a small brush which may be used, for example, to collect a sample of epithelium. The curette 44 has an axial length less than the length of the container 10, so that curette 44 may be placed entirely within the container and the lid 18 screwed in place sealably to enclose the curette within the container, as suggested in FIG. 2. The curette 44 shown in the figures may comprise a small portion detachable from the distal end of a longer handle portion (not shown). A longer handle portion permits the collection of a sample from within a patient's body, e.g., from the cervix, and thereafter the curette 44 bearing the specimen is detached and deposited in the container 10.

The chamber 20 is used in conjunction with a filter card 40, which has a shape generally corresponding to a filter recess 41 on the exterior of the flange 26 and surrounding the discharge opening 30. Filter card 40 has central aperture 42 therethrough in a generally conventional manner. The filter recess 41 receives and holds the filter card 40 in position across the discharge opening 30 while the invention is in use. Filter card 40 features at least one, and preferably two, notches 43, 43' therein, preferably one each on the top and bottom edges of the filter card 40. Keys 45, 45' furnished on the flange 26 extend into the filter recess 41 and are alignable with the notches 43, 43'. Keys 45, 45' are insertable into respective notches 43, 43' properly to align the filter card 40 within the filter recess 41 and upon the flange 26. Additionally and advantageously, the border portions of the filter card 40 on each side of each of the notches 43, 43' exert an extra capillary force to pull fluid from the center of the filter card 40 toward the corners of the filter to promote a more even distribution of cellular matter across the filter card 40.

The gasket 46 seals the chamber 20 to a conventional microscope slide 50. The gasket 46 preferably comprises a planar section of closed-cell foam material, rectangular in shape and sized to cover the exterior surface of the flange 26. The gasket 46 has a rectangular opening 48 therethrough matching in size and positioned to register with the aperture 42 and discharge opening 30. With the filter card 40 positioned within the filter recess 41, the gasket 46 is preferably bonded or otherwise permanently adhered to the flange 26, thus holding the filter card in place between the gasket and the flange. The gasket 46 when permanently affixed to the chamber 20 discourages furtive or accidental re-use of the chamber, which is undesirable for reasons of contamination.

The chamber 20 with slide 50, gasket 46 and filter card 40 attached is releasably installed for use within a cytocentrifuge in a conventional manner, for example as explained in U.S. Pat. No. 5,470,758. Advantageously, the container 10 enclosing the specimen also remains connected to the chamber 20 during centrifugation.

In all preferred embodiments of the invention, the chamber 20 and the container 10 preferably are molded from an inexpensive inert plastic so as to be disposable and to allow the chamber 20 and container 10 to be discarded after a single use.

The method of the invention permits centrifugation analysis on a biological material sample conveniently and with a reduced risk of contamination. At the point of specimen collection, such as a physician's office, the user need immediately possess only the container 10, lid 18, and curette 44. The user collects the biological material sample using the curette 44. The user then places the curette 44, with the biological material sample thereon, into the container 10. In the preferred method, the user then places a liquid solution 11 into the container 10 to preserve the sample and create a liquid suspension of the sample. The liquid solution utilized is any of the liquids, typically including alcohol, known in the art of preparing cellular samples, such as epithelial samples, for centrifugation and microscopic analysis. Once the liquid solution 11 has been placed into the container 10, preferably in sufficient volume to substantially or completely immerse the curette 44, the user secures the lid 18 to the top of the container 10 by twisting the lid onto the container to engage the threads 19 of the lid with the threads 14 of the container. The threaded connection between the lid 18 and the container 10 secures the lid in place and provides a sealed barrier to leakage and contamination.

The sealed container 10, with the curette 44 therein, then is transported to the laboratory for centrifugation. Notably, the container 10 remains closed during transport, regardless of whether the laboratory is in a room adjoining the point of collection, or hundreds of miles away.

In the laboratory, the container, with the curette 44 remaining therein, is attached to the sample chamber 20. The user removes the lid 18 from the container 10 and immediately twists the top of the container 10 into the port 28 to engage the threads 14 of the container 10 with the threads 29 of the port 28. Preferably, the container 10 is attached to the chamber 20 by maintaining the container 10 upright (open top end 13 up), inverting the chamber 20 and aligning the port 28 with the top of the container 10, and rotating either the chamber 20 or the container 10 to engage the threads 14, 29. By screwing the port 28 onto the container 10, the user attaches the container 10 to the chamber 20 with the top of the container aligned with the inlet 24 of the holding portion 22. In this fashion, the liquid sample solution remains safely within the container 10 until a complete, sealed attachment of the container 10 to the chamber 20 has been realized.

After thus attaching the container 10 to the chamber 20, the container is inverted and the chamber 20 reverted to the relative positions suggested in FIG. 1. With the container 10 in sealed attachment to the chamber 20, the liquid within the container is allowed to flow freely by gravity from the container, through the inlet 24, and into the holding portion 22, thus permitting the liquid to pass from the container to the chamber. As the liquid passes into the chamber 20, it carries with it biological material washed from the curette 44, thereby carrying the material into position for centrifugation through the filter card 40 and to a microscopic slide 50, according to known centrifugation methods. The container 10 with any curette 44 used therein, remains securely attached to the chamber 20 during centrifugation.

The container brace 32 contacts the container 10 while the container 10 is in the attached position. Brace 32 assists in maintaining the container in attached position, particularly buttressing the container from accidental lateral blows and also supporting the container against the centrifugal force during centrifugation.

Persons of skill in the art readily will appreciate that the inventive method may be advantageously practiced without the use of a curette 44, for example, in the case of a blood sample drawn using a hypodermic syringe. Thus, in an alternative method of the invention, the practitioner using a sterile syringe draws a blood sample, then immediately deposits the sample from the syringe into the container 10, and preferably adds a preservative solution 11 or other indicated liquid. The lid 18 is then secured to the container 10, and the container transported and attached to the chamber 20 as previously described. Upon inverting the container 10, the blood sample passes into the chamber 20 preparatory to centrifugation.

The advantages of the invention are manifest to be a decreased opportunity for confusion or contamination of samples, as well as more efficient preparation of samples for centrifugation. Notably, samples collected upon a curette 44 are protected from contamination virtually from the time of collection to the instant they are placed within the centrifuge. The invention removes the need to pass unprotected specimen material from the curette 44 to any intermediate containers or surfaces preparatory to centrifugation. Rather, the original curette 44 bears the specimen from collection to centrifugation, all the while protected within a single container 10. The container 10 is adapted to attach directly to the sample chamber itself, thus obviating the need to employ a pipette or funnel to transfer the specimen from the curette 44 to the centrifuge sample chamber 20. Eliminating intermediate transfers of material dramatically reduces the possibility that an unclean pipette or slide will contaminate the specimen prior to centrifugation. Similarly, since multiple containers are not used to move the specimen from point of collection to point of centrifugation, the possibility of specimen mix-ups is curtailed. It is also to be appreciated by persons skilled in the art that the invention will promote efficient, rapid use of the centrifuge in laboratory analysis.

It is therefore to be understood that while preferred forms and methods of the invention have been herein set forth and described, various modification and changes may be made in the construction and arrangement of parts, composition of materials, and order of steps without departing from the spirit and scope of the present invention as defined by the appended claims.

What is claimed is:

1. A method of transferring a biological material sample to a microscope slide for analysis, comprising:
   providing a container having an open end;
   depositing the sample within the container;
   supplying an inlet in an outside wall of a sample chamber in communication with the microscope slide;
   securing the open end of the container to the inlet for introduction of the sample into the chamber; and
   centrifuging the chamber and container to cause the sample to pass from the container through the chamber onto the microscope slide.

2. The method of claim 1 wherein said container has a threaded open end, and further comprising supplying a lid having threads engageable with said threaded open end.

3. The method of claim 2 further comprising screwing the lid onto the open end of the container subsequent to depositing the sample within the container.

4. The method of claim 1 wherein depositing the sample within the container comprises:
   collecting the sample upon a curette; and
   placing the curette within the container.

5. The method of claim 4 further comprising placing a liquid into the container prior to securing the container to the chamber.

6. The method of claim 1 wherein the inlet is provided with threads engageable with the open end.

7. The method of claim 6 wherein securing the container to the chamber comprises screwing the chamber onto the open end of the container.

8. The method of claim 1 further comprising advancing said sample along a tortuous path in said chamber and discharging through a filter card onto said microscope slide.

9. The method of claim 8 further comprising:
   providing a filter card having at least one notch therein;
   furnishing a key upon the chamber; and
   aligning the notch with the key.

10. The method of claim 9 further comprising placing said filter card between a gasket and the chamber.

11. In a system for transferring a biological material sample to a cytological centrifugation sample chamber wherein said chamber includes a discharge opening in communication with a microscope slide, the improvement comprising:

a container having an openable end for placing said sample in said container;

an external inlet port on said chamber; and means for securing said container to said inlet port whereby to introduce said sample from said container through said inlet port into said chamber.

12. In a system according to claim 11 wherein said container is provided with means for securing a lid thereto.

13. In a system according to claim 12 wherein said securing means includes threads on said openable end, and said lid comprises threads engageable with said threads on said openable end.

14. In a system according to claim 12 further comprising a curette disposable within said container.

15. In a system according to claim 13 wherein said container is inverted with said openable end in threaded engagement with said inlet port and wherein said inlet port and said container incline upwardly from said chamber.

16. In a system for transferring biological material sample to a cytological centrifugation sample chamber of the type having an inlet at one end and a discharge end in communication with a microscope slide, the improvement comprising:

a container having an open end;

a lid for removably closing said open end;

complementary screw threads upon said, container and upon said lid;

an inlet port mounted externally said sample chamber in communication with said inlet including screw threads complementary to said threads on said container; and a solution and a curette containing said sample disposable within said container whereupon removal of said lid and threaded engagement of said port with said container, said sample flows with said solution into said chamber.

17. In a system according to claim 16 further comprising:

a filter card having a central opening and at least one notch therein; and a key in said discharge end complementary to said notch and alignable with said notch.

18. In a system according to claim 17 further comprising a gasket permanently affixing said filter card to said discharge end.

* * * * *